United States Patent [19]

Neuman

[11] Patent Number: 5,057,275
[45] Date of Patent: Oct. 15, 1991

[54] ANALYTIC READER DEVICE

[75] Inventor: Robert G. Neuman, Philadelphia, Pa.

[73] Assignee: Exocell, Inc., Philadelphia, Pa.

[21] Appl. No.: 245,423

[22] Filed: Sep. 16, 1988

[51] Int. Cl.$^5$ .......................................... G01N 21/01
[52] U.S. Cl. ...................................... 422/55; 422/58; 422/68.1; 422/102
[58] Field of Search .................. 422/55, 58, 102, 68.1; 436/165; 73/865.8; 356/423

[56] References Cited

U.S. PATENT DOCUMENTS

| | | | |
|---|---|---|---|
| D. 185,543 | 6/1959 | Frank | D16/2 |
| D. 186,271 | 10/1959 | Marks | D16/2 |
| D. 247,821 | 5/1978 | Biersch et al. | D24/17 |
| D. 250,834 | 1/1979 | Ruppert | D24/1.1 |
| D. 256,567 | 8/1980 | Voss et al. | D10/81 |
| 437,800 | 10/1890 | Robinson | 116/285 |
| 1,675,967 | 7/1928 | Zitkowski | 356/412 |
| 2,027,816 | 1/1936 | Drunker | 88/14 |
| 2,146,005 | 2/1939 | Bernholz et al. | 116/135 |
| 2,353,716 | 7/1944 | Estey et al. | 356/40 |
| 3,176,577 | 4/1965 | Frank | 88/14 |
| 3,381,572 | 5/1968 | Tuwiner | 83/14 |
| 3,488,156 | 1/1970 | Good et al. | 23/253 |
| 3,591,805 | 7/1971 | Schoeffel | 250/71 R |
| 3,713,985 | 1/1973 | Astle | 23/253 R |
| 3,721,010 | 3/1973 | Ristow | 116/129 R |
| 3,964,831 | 6/1976 | Frank | 356/182 |
| 4,056,359 | 11/1977 | Janin | 435/301 |
| 4,073,623 | 2/1978 | Bodart | 23/259 |
| 4,330,299 | 5/1982 | Cerami | 23/230 |
| 4,468,371 | 8/1984 | Chen et al. | 422/102 |
| 4,594,327 | 6/1986 | Zuk | 436/514 |
| 4,678,757 | 7/1987 | Rapkin et al. | 436/169 |
| 4,871,258 | 10/1989 | Herpichboehm et al. | 356/422 |
| 4,877,580 | 10/1989 | Aronowitz et al. | 422/58 |
| 4,904,605 | 2/1990 | O'Brien et al. | 436/169 |
| 4,923,800 | 5/1990 | Ly | 422/58 |
| 4,956,302 | 9/1990 | Gordon | 436/161 |

FOREIGN PATENT DOCUMENTS

| | | |
|---|---|---|
| 818270 | 1/1951 | Fed. Rep. of Germany . |
| 824554 | 2/1938 | France . |

Primary Examiner—Richard V. Fisher
Assistant Examiner—Charles K. Friedman
Attorney, Agent, or Firm—Banner, Birch, McKie & Beckett

[57] ABSTRACT

An analytical reader device having an elongated fixed standard tray supporting thereon a strip of standard wells and an elongated movable sample tray supporting thereon a strip of sample wells. A track arrangement connects and allows the movable sample tray to slide along the fixed standard tray. A rack gear is secured along the side of the movable sample tray opposite to the track arrangement. A geared dial is rotatably supported on a support plate secured to the fixed standard tray. The teeth of the geared dial mesh with the teeth of the rack gear so that as the movable sample tray slides the dial rotates. When a sample well is positioned adjacent the visually similar standard well, the dial is turned so that the correct concentration reading thereon appears through a fixed readout window.

21 Claims, 4 Drawing Sheets

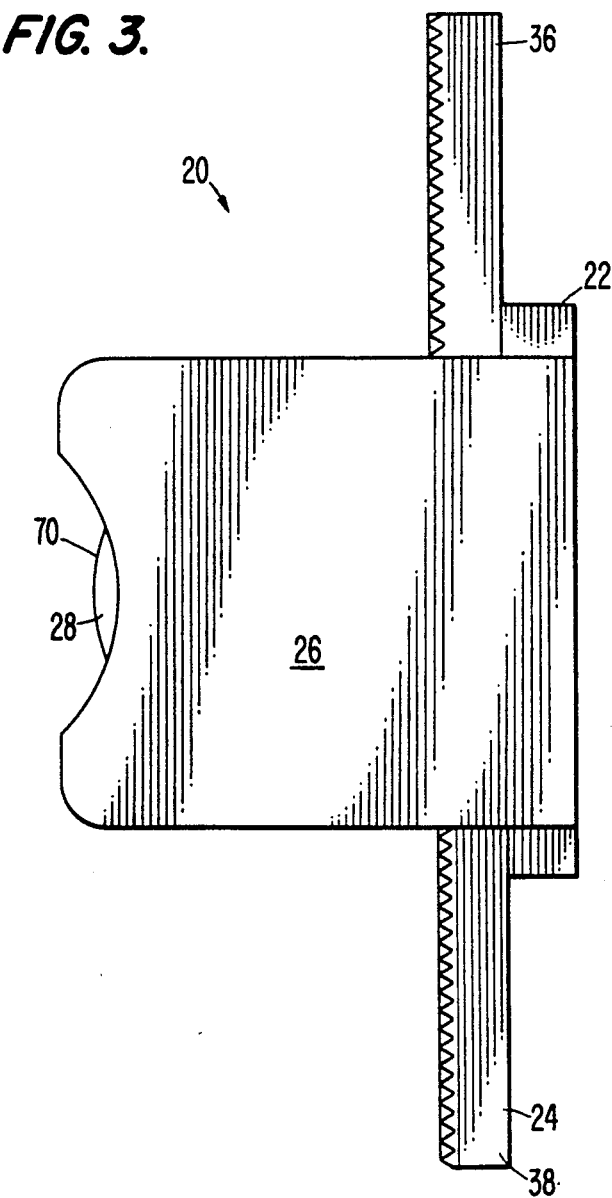
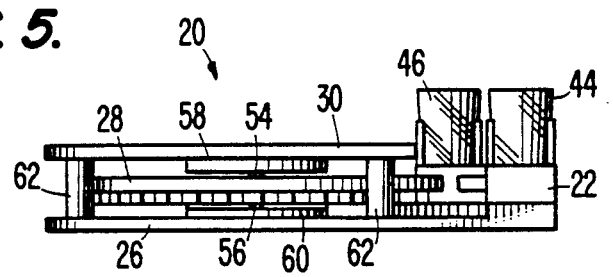
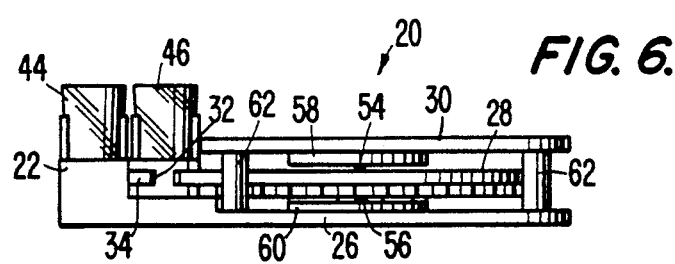

ANALYTIC READER DEVICE

BACKGROUND OF THE INVENTION

The present invention is directed, in general, toward test apparatus and, more particularly, toward apparatus for determining the presence of an analyte in a sample.

Recently, various methods have been developed for detecting a variety of analytes in samples where the analyte is capable of reacting with a reagent to produce a particular color or hue. The color which is produced can, in turn, be detected as, for example, by using a spectrophotometric instrument. These prior devices typically are complicated and involve electronic components and do not allow for the variation in testing conditions. More particularly, many devices are known which match the colors of an unknown test sample in serial dilution with those of known concentrations of an authentic standard.

Some of the techniques which have become increasingly useful in detecting an analyte in a sample use antibodies. In these techniques the antibody is used to detect the presence of the analyte, in this case an antigen, for which the antibody is specific. Over the last several years, the sensitivity of antibody-based tests have increased such that less liquid volume is required enabling the use of the microtiter plates.

SUMMARY OF THE INVENTION

Accordingly, it is a principal object of the present invention to provide an improved device for determining the presence of an analyte in a sample.

A further object of the present invention is to provide such an improved device which is easy construct, inexpensive to manufacture, can be handheld, does not involve any expensive or complicated electronic components, and which automatically and accurately indicates the concentration of the sample.

The present invention is directed to achieving these objects. It provides an elongated stationary standard tray having spaced post-type holders into which the end wells of a strip of interconnected standard wells are attached. Along the inside edge of the stationary sample tray is an elongated track in which an elongated movable standard tray slides. The movable sample tray similarly has holder devices at spaced locations for holding therein a strip of interconnected sample wells. In a preferred embodiment the elongated movable sample tray has a rack gear along its inside edge, and a circular gear attached to a dial meshes with the gears of the rack gear. A support plate secured to the stationary standard tray is positioned on the side of the movable sample tray opposite to the stationary standard tray. The dial then is mounted for rotation about an axis through this support plate. Thus, as the movable sample tray is moved in the track the dial will be caused to rotate as its gears mesh with the gears of the rack. Numbers corresponding to the concentration of the substance to be tested and placed in the wells of the movable sample tray are imprinted radially on the dial. Then as the movable sample tray is moved relative to the stationary standard tray so that the wells of the sample tray having substances of the same visual appearance as those in the standard tray are aligned adjacent one another, the dial is automatically rotated by the meshing gears. When in this aligned position one of the numbers on the dial appears in a window of the face plate covering the dial. This number then is the concentration of the tested substance.

Other objects and advantages of the present invention will become more apparent to those persons having ordinary skill in the art to which the present invention pertains from the foregoing description taken in conjunction with the accompanying drawings.

BRIEF DESCRIPTION OF THE DRAWINGS

FIG. 3 is a bottom plan view of the device of FIG. 1.

FIG. 5 is a top end elevational view of the device of FIG. 1.

FIG. 6 is a bottom end elevational view of the device of FIG. 1.

DETAILED DESCRIPTION OF PREFERRED EMBODIMENTS OF THE PRESENT INVENTION

Figure 1:
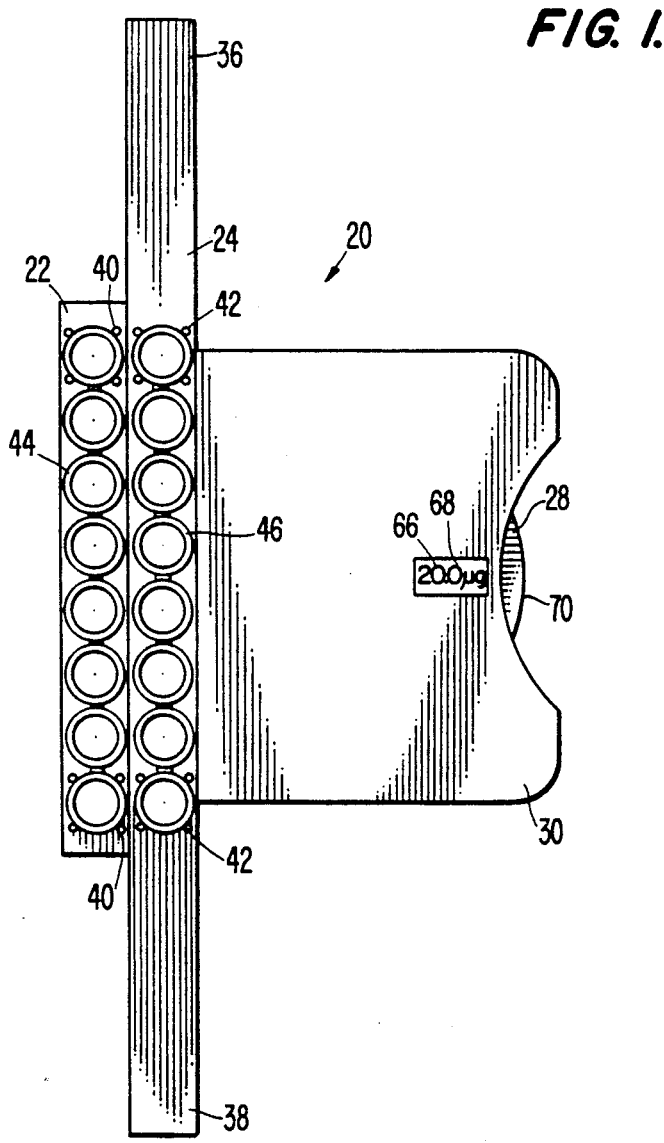
FIG. 1 is a top plan view of a first analytic reader device of the present invention.
Figure 2:
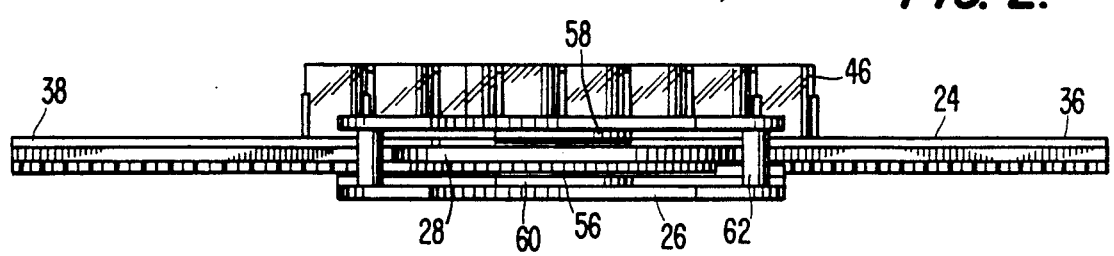
FIG. 2 is a right side elevational view of the device of FIG. 1.
Figure 4:
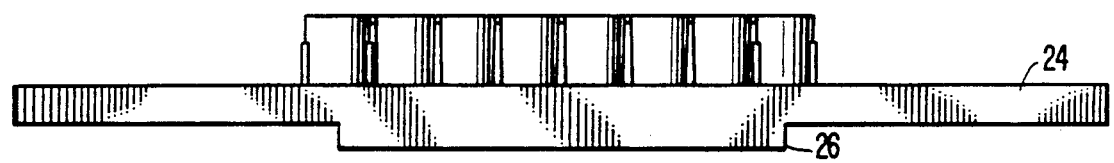
FIG. 4 is a left side elevational view of the device of FIG. 1.

As mentioned above, the present invention is directed toward apparatus and method for detecting the presence of an analyte in a sample. Generally, two strips having microtiter wells are provided for performing the subject analyte detection tests. A standard strip contains a known concentration of the analyte to be detected and the sample strip contains the sample which may contain the analyte.

The term "analyte" as used herein denotes the substance which is being detected in the sample and can be either inorganic or organic in its composition.

The term "color" as used herein is meant to denote a change in the light absorbance or intensity occurring due to the interaction of analyte with the analyte detection reagents. As such, the term, as used herein, would also include changes in the shade of color.

The nature of the test used to detect the presence of the analyte will vary depending on the analyte and may be based, for example, on classical chemical or immunological detection techniques. Such tests are known to those of skill in the art.

Particularly preferred tests for detection of analyte are those based on immunoassay techniques utilizing analyte-specific antibody.

The term "antibody" as used in this invention is meant to include intact molecules as well as fragments thereof, such as, for example, Fab and F(ab')$_2$, which are capable of binding the analyte.

Antibodies are particularly suited for use in immunoassays in which they can be utilized in liquid phase or bound to a solid phase carrier. In addition, the antibodies in these immunoassays can be detectably labeled in various ways. Examples of types of immunoassays which can utilize antibodies are competitive and noncompetitive immunoassays in either a direct or indirect format. Examples of such immunoassays are the radioimmunoassay (RIA) and the sandwich or other format (immunometric) assay. Detection of analyte using antibodies can be done utilizing immunoassays which are run in either the forward, reverse, or simultaneous modes, including immunohistochemical assays on physiological samples. Regardless of the type of immunoassay which is used, the concentration of antibody utilized can be readily determined by one of skill in the art.

Depending on the nature of the immunoassay the analyte specific antibody can be bound to many different carriers and used to detect the presence of analyte. Examples of well-known carriers include glass, polystyrene, polyvinyl chloride, polypropylene, polyethylene, polycarbonate, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding antibody, or will be able to ascertain such, using routine experimentation.

The specific concentration of antibody, the temperature and time of incubation, as well as other assay conditions, can be varied depending on such factors as the concentration of the antigen in the sample, the nature of the sample, and the like. Those skilled in the art will be able to determine operative and optimal assay conditions for each determination while employing routine experimentation. For example, the immunoassay may be run at about 4°-45° C., preferably at about 26° C., and each incubation step may be as long as 4 hours or more, although much shorter times, for example, about 10 minutes is preferred.

Other steps such as washing, stirring, shaking, filtering, or pre-assay extraction of analyte and the like may, of course, be added to the assays, as may be desired or necessary for a particular situation.

Depending on the particular immunoassay, one or more of the antibodies will be coupled with, or modified to produce, a detectable label. Such substances to which the antibody can be coupled include enzymes and fluorescent compounds.

Those of ordinary skill in the art will know of other suitable labels for binding to the antibody, or will be able to ascertain such using routine experimentation. Furthermore, the binding of these labels to the antibody can be done using standard techniques common to those of ordinary skill in the art. One of the ways in which the antibody in the immunoassay can be detectably labeled is by linking this binding partner to an enzyme. This enzyme, in turn, when later exposed to its substrate will react to the substrate in such a manner as to produce a chemical moiety which can be visually detected. Examples of enzymes that can be used to detectably label are horseradish peroxidase, malate dehydrogenase, staphylococcal nuclease, delta-5-steroid isomerase, yeast alcohol dehydrogenase, alpha-glycerophosphate dehydrogenase, triose phosphate isomerase, alkaline phosphatase, asparaginase, glucose oxidase, betagalactosidase, ribonuclease, urease, catalase, glucose-6-phosphate dehydrogenase, glucoamylase, and acetylcholine esterase.

It is also possible to detect the presence of the analyte by labeling the antibody with a fluorescent compound. When the fluorescently labeled antibody is exposed to light of the proper wavelength, its presence can then be visually detected due to fluorescence of the dye. Among the most important fluorescent labeling compounds are fluorescein isothiocyanate, rhodamine, phycoerythrin, phycocyanin, allophycocyanin, o-phthaldehyde, and fluorescamine.

For purposes of the invention, the analyte which is being detected may be present in biological fluids and tissues, as well as samples derived from environmental and ecological sources.

Any sample containing a detectable yet unknown amount of analyte can be used. Thus, the sample can be liquid such as, for example, urine, saliva, cerebrospinal fluid, blood, serum, water and the like, or a solid or semi-solid such as, for example, tissues, feces, plant material, inorganic substrates, feeds and the like. Among the analytes which can be detected are hormones, enzymes, inflammatory agents, infectious agents, and toxins, as well as such environmental contaminants as pesticides, herbicides, pollutants, or other such compounds.

Hormones are substances that act to inhibit or enhance metabolic activities. Examples of hormones of interest are those associated with reproduction such as human choriogonadotropin, luteinizing hormone and follicle-stimulating hormone, as well as hormones associated with metabolism, such as thyroid-stimulating hormones and the like.

Enzymes are protein molecules which catalyze biochemical reactions. Changes in the concentration of enzymes which are associated with certain biochemical pathways can be of valuable diagnostic significance in evaluating a disease state. Examples of enzymes of significance are most protein kinases, creatinine phosphokinase, lactate dehydrogenase, C reactive protein (CRP), serum amyloid P component (SAP), alpha-2 macroglobulin, and the like.

Inflammatory agents can be released by cells of the immune system, often following contact with an antigen. Examples of inflammatory agents include histamine, prostaglandins, thromboxane, herparin, tryptase, kininogenase and beta-glucosaminidase.

Infectious agents primarily encompass disease-causing organism of viral, bacterial or parastic origin. Examples of such agents are those causing dengue fever, bubonic plague, yellow fever, malaria, small pox, pneumonia and encephalitis.

Toxins are poisonous substances some of which are produced by plants, animals, or microorganisms that in sufficient dose can be debilitating or lethal. Examples of such toxins are botulin, zearalenone and Bacillus thuringiensis toxin.

Environmental contaminants which can be detected are pesticides, for example, diflurbenzuron, paraquat, and aldicarb sulfone; herbicides, for example, 2,4-D, alachlor, glyphosate, chlorpyrifos, and atrazine; as well as such pollutants as, for example, dioxin and polychlorinated biphenyls.

Figure 7:
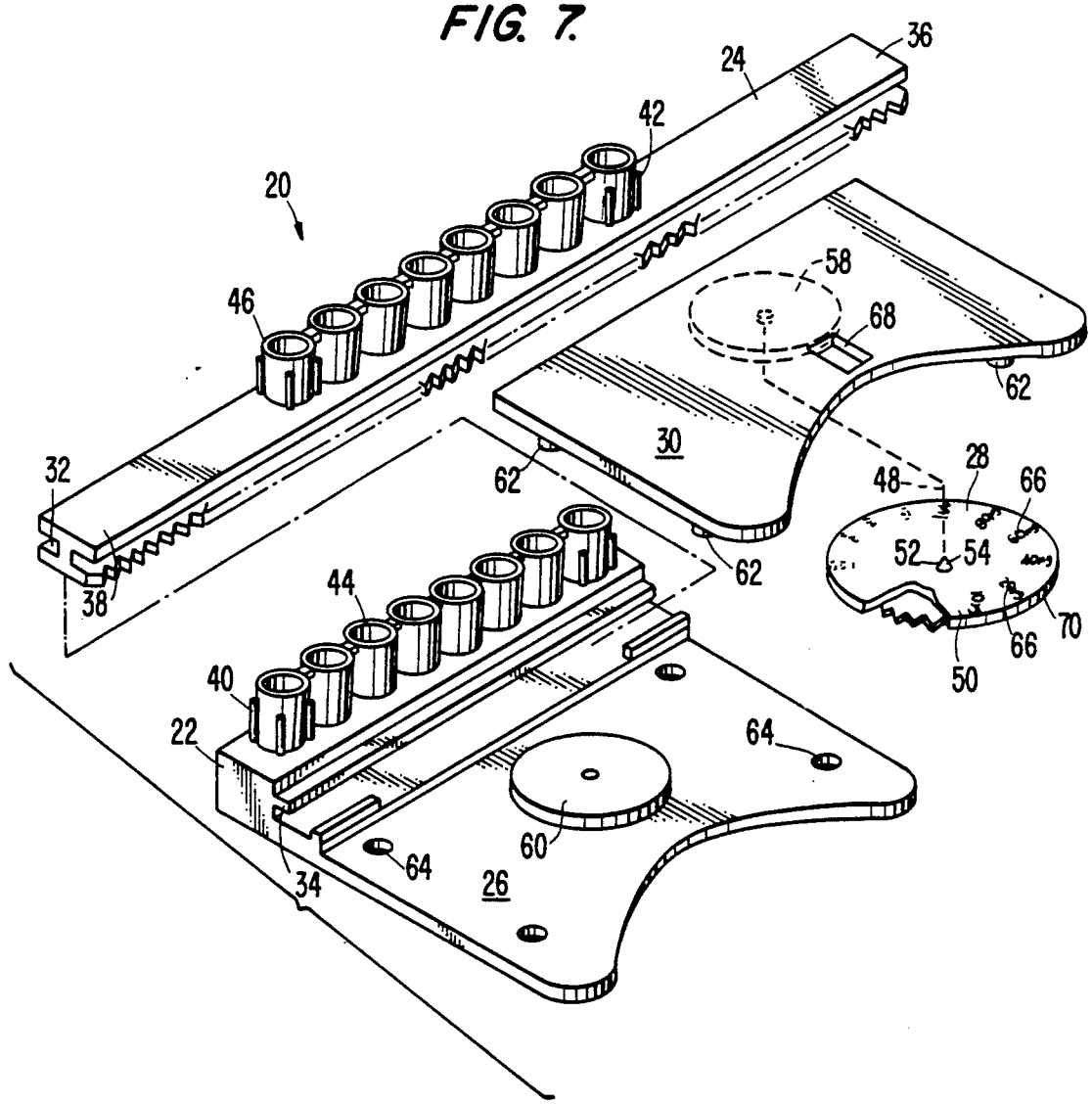
FIG. 7 is a top perspective view of the device of FIG. 1 having components thereof illustrated in exploded relation.
Figure 8:
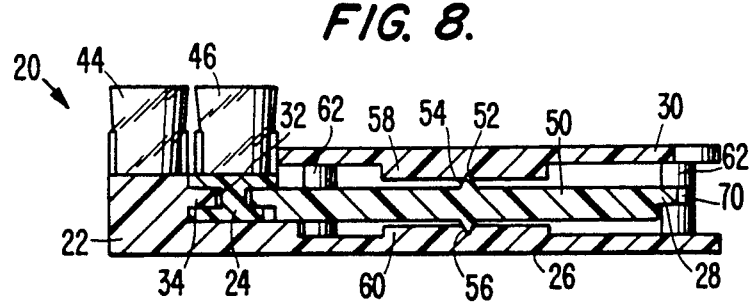
FIG. 8 is a lateral cross-sectional view of the device of FIG. 1.

Referring to FIGS. 1 and 7 an analytic reader device of the present invention is shown generally at 20. Device 20 is seen to basically comprise a stationary standard tray 22, a movable sample tray 24, a support plate 26, a dial 28, and a face or cover plate 30. The movable sample tray 24 has along its outside edge an elongated track 32 in which the elongated side engaging member 34 of the stationary standard tray 22 rides. The movable sample tray 24 is longer at either end 36, 38 thereof than is the stationary standard tray to extend the corresponding track 32 of the movable sample tray 24 which must be moved the length of the stationary standard tray 22. Both the stationary standard tray 22 and the movable sample tray 24 have four round post-type holder members thereon 40, 42 spaced so as to retain therein the opposite end wells of strips of wells 44, 46. These holders 40, 42 are adapted so that the strips of wells 44, 46 can be easily snapped in and out for replacement purposes. The holder posts are each moved in the distance of one well where a six instead of an eight well strip is to be used. Although it is preferred to not have fewer than six wells, as few as three can be used. The strips 44, 46 are preferably removable microtiter strips which are commercially available and are pretreated and disposable. The holders 40 of the stationary standard tray 22 will hold a strip of wells 44 holding serially diluted solutions of the standard. Likewise, the holders 42 of the movable sample tray 24 will hold a strip of wells 46 containing the sample fluid in serial dilution. The techniques for preparing these dilutions are known and are also set forth herein.

The support plate 26 is secured relative to the stationary standard tray 22, as best shown in FIG. 7, and the axis 48 of the dial 28 passes perpendicularly therethrough. The dial 28 is shown to comprise a disk 50 with an axle 52 at the axis 48 through the center thereof with pointed tips 54, 56 at either end of the axle 52. These tips 54, 56 then, when the dial 28 is secured in the device, are held and rotate in circular rotation plates 58, 60 as shown in FIG. 7. The cover plate 30 has four posts 62 secured thereto and extending down therefrom which removably snap into four openings 64 in the support plate 26. This allows the cover plate 30 to be removed so that the dial 28 can be replaced as needed as will be apparent from the discussion to follow.

The dial 28 has about it spaced numbers 66 representing the possible concentrations of the substance to be tested and associated with those in the standard wells. These numbers 66 can be positioned to be facing radially out from the center of the dial or can be positioned to be along the radii of the dial (as depicted in FIG. 7). Where more than one substance (analyte) is to be tested then a different set of numbers (not shown) can be provided in a circular band concentric to the band of the first set of numbers 66. The cover plate 30 has a window 68 therethrough through which one or possibly two numbers 66 on the dial 28 are visible depending upon the orientation of the dial 28 about its axis 46. This window 68 can be at any position relative to the dial 28 and is shown in the drawings at the three o'clock position but it also could be at, for example, the six or nine or twelve o'clock positions. In lieu of the window 68 an indicator arrow (not shown) can be provided such as on the face plate 30 to indicate which of the values or numbers 66 on the dial 28 is the correct value for that test solution. A different dial can be inserted with a different set of readout concentrations thereon to accommodate different assays.

Thus, the procedure for determining the concentration is very easy. The standard and sample wells are prepared with the serially diluted solutions as is known. The strips of wells 44, 46 are oriented relative to the trays so that the concentration increases from the top to the bottom and then snapped into place in their respective holders 40, 42. The movable sample tray 24 then is moved along the track 30 so that the sample and standards wells are positioned adjacent one another when the visual characteristics thereof are identical. These visual characteristics can be color, color intensity, trubidity, opaqueness, or any other visually detectable parameter that changes in relation to the concentration of a test substance. It can be used for absorbance of light in the visible spectrum or under ultra violet light for fluorometric assays. The device 20 can be utilized in any assay where the retention, generation or alteration of a substance that emits or absorbs light in the visible spectrum as correlated, directly or inversely, with the concentration of the test substance.

The movable sample tray 24 can be manually juxtaposed by moving, as with the tester's thumb, the edge 70 of the dial 28 extending out from between the support and cover plates 26, 30 as shown in FIG. 1. In other words, it is manually juxtaposed until the color range of the sample strip 46 aligns with that of the standard strip 44. At each alignment station, the concentration of the test substance, which is precalculated for the test in use and printed on the dial 28 as shown by numbers 66, appears in the window 68 on the face plate 30.

Alternatively, in lieu of the stationary strip of standard wells 44, a color graduated polymer strip (not shown) of paper, plastic, nitrocellulose and the like can be used. The removable standard well technique, though adding an additional preparation technique to this reading device, is more accurate since the solutions in the standard wells and the sample wells are prepared under similar testing conditions including the same temperature of the reagent.

Figure 9:
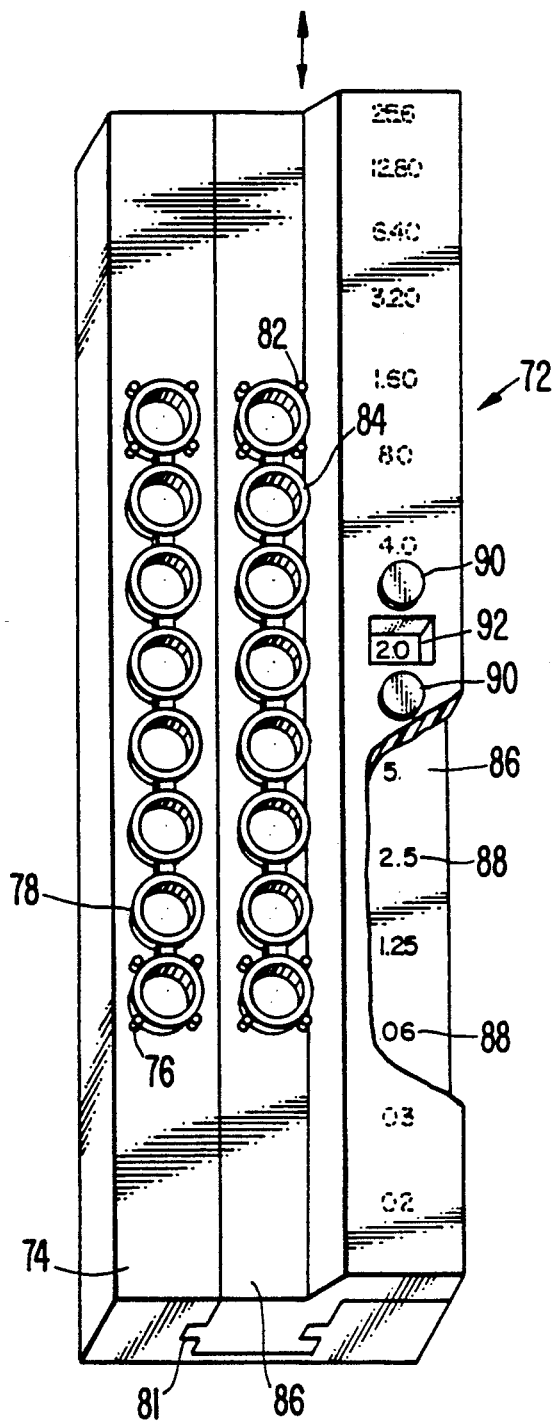
FIG. 9 is a top perspective view of a second analytic reader device of the present invention.
Figure 10:
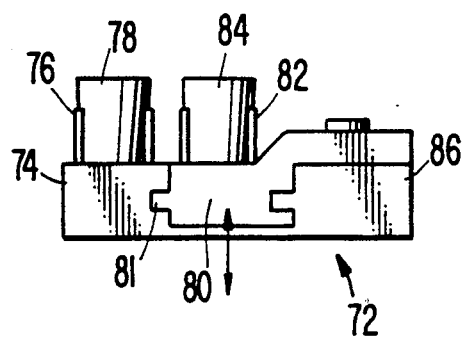
FIG. 10 is an end elevational view of the device of FIG. 9.

A second design of the analytic reader device of the present invention is shown generally at 72 in FIGS. 9 and 10. Referring thereto it is seen that a similar elongated stationary standard tray 74 is provided with holding posts 76 for holding the strip of standard wells 78. The elongated movable sample tray 80 then slides in a track 81 along the stationary standard tray 74 and the movable sample tray 80 similarly has holding posts 82 for snap holding a strip of sample wells 84. On the side of the movable sample tray 80 opposite to and underneath the stationary standard tray 74 is an elongated strip 86 fixed relative to the stationary standard tray 74. The various possible concentrations 88 are imprinted along this strip 86. The sliding sample tray 80 can be slid relative to the stationary standard tray 74 to juxtapose or match visually identical standard and sample wells by grasping the finger grips 90. A readout window 92 is provided so that when the sample and standard wells are manually aligned the readout window 92 then is positioned directly over the correct numerical value 88 on the strip 86. This numerical value can then be easily read.

For both of these embodiments 20, 72 where the readout window 68, 92 or indicator arrow does not fall precisely on a printed concentration number than the value can be estimated between the two nearest numbers. Where different substances involving different concentration values are to be tested then a different strip 86 or a different dial 28 having corresponding different numerical values on it can be easily substituted. It is also within the scope of this invention to reverse the operation of this device so that the standard wells move or slide relative to the sample wells.

Accordingly, this device is inexpensive to manufacture and operate and can be easily held in the hand of the tester. The visual comparison can be easily done and the value then quickly read.

The above disclosure generally describes the device of the invention. A more complete understanding can be obtained by reference to the following example which is provided herein for purposes of illustration only and is not intended to limit the scope of the invention.

EXAMPLE 1

Detection of Albumin in Urine Specimens

The standard and sample microtiters well strips were coated with human serum albumin (HSA) wherein 500 ng HSA/well was immobilized using a coupling buffer consisting of 54 mM NaCl, 45 mM Glycine and 0.05% sodium azide, pH 8.4. The strips were incubated for at least two hours at ambient temperature, after which non-specific binding sites were blocked by the addition of coupling buffer containing 0.1% BSA, followed by incubation at room temperature for at least one hour. The strips were then washed four times with phosphate buffered saline (PBS) containing 0.05% Tween 20 (SIGMA).

Next, the standard and sample strips 44, 46 were placed into well holders 40, 42 and 100 ul of diluent phosphate buffered saline, pH 7.4, 0.1% bovine serum albumin) added to all eight wells of both strips. After the addition of diluent, 100 ul of a standard solution containing 20 ug/ml HSA was added to the first well of the standard strip. Starting with this well the albumin standard is then serially diluted through the remaining wells of the standard strip and 100 ul discarded from the last well.

Prior to the addition of urine to the sample strip the urine specimen was clarified by centrifugation. Next, 100 ul of clarified urine was added to the first well of the sample strip 46. The contents of the wells were then serially diluted in 100 ul aliquots through the remaining wells of the sample strip 46 and 100 ul discarded from the final well thereof.

After the standard and sample has been serially diluted 100 ul containing a 1:5000 dilution of horseradish peroxidase conjugated-goat anti-human albumin (GAA-HRP) (Cappel Laboratories) was added to all of the wells on both strips 44, 46 and incubated at room temperature for ten minutes.

After completion of the incubation step, all of the wells were washed six times with water, preferably distilled water, and 100 ul of o-phenylenediamine (OPD, Sigma) in 0.1M dibasic sodium phosphate, 0.5M citric acid and 1 ul/ml of 30% hydrogen peroxide at pH 5.0, was added to all of the wells on both the standard and sample strips 44, 46 and incubated at room temperature for two minutes. Finally, the reaction was stopped by the addition of 100 ul of two M sulfuric acid to all of the wells on both the standard and sample strips. The color was stable for several hours.

In order to determine the concentration of albumin in the urine sample the standard strip 44 was mounted on the left stationary plate 22 of the device 20 such that the top and bottom wells were contained in the well holders 40. In this configuration it was important that the first well, containing the highest concentration of standard, was positioned at the top of the device.

Next, the sample strip 46 was mounted on the right movable plate 24 of the device, taking the same precautions as those exercised with the standard strip. When both strips 44, 46 were adjacent from top to bottom the concentration value 66 indicated in the window 68 of the device read twenty ug/ml. Finally, in order to determine the concentration of albumin in the sample diluted in the sample strip wells, the dial 28 of the device of the invention was moved clockwise or counterclockwise until the color in the sample wells matched, well-for-well, with the color in the adjacent wells of the standard strip. The numerical concentration as shown in the window 68 was then read. In those instances where values in-between the printed concentrations were obtained it was possible to estimate the concentration in the sample.

In this particular immunodiagnostic configuration a competitive immunoassay was used such that the concentration of albumin was inversely related to color which, under the conditions described herein, were shades of orange since OPD was the substrate.

Table 1 shows the results of using the device of the invention and compares the values obtained for the standard strip as compared to a sample strip containing normal human urine and a sample strip containing normal human urine to which human serum albumin (HSA) had been added (75 ug/ml).

TABLE 1

| STANDARD STRIP BUFFER & HSA | | | SAMPLE STRIP | | | | | |
|---|---|---|---|---|---|---|---|---|
| | | | NORMAL URINE | | | NORMAL URINE & HSA | | |
| WELL | COLOR | [HSA][a] | WELL | COLORS[b] | [HSA][a] | WELL | COLOR[b] | [HSA][a] |
| — | — | — | — | — | — | 1 | no color | — |
| — | — | — | — | — | — | 2 | no color | — |
| 1 | no color | 20 | — | — | — | 3 | no color | 20 |
| 2 | very light | 10 | — | — | — | 4 | very light | 10 |
| 3 | light | 5 | 1 | light | 5 | 5 | light | 5 |
| 4 | medium light | 2.5 | 2 | medium light | 2.5 | 6 | medium light | 2.5 |
| 5 | medium | 1.25 | 3 | medium | 1.25 | 7 | medium | 1.25 |
| 6 | medium dark | 0.63 | 4 | medium dark | 0.63 | 8 | medium dark | .63 |
| 7 | dark | 0.31 | 5 | dark | 0.31 | — | — | — |
| 8 | very dark | 0.16 | 6 | very dark | 0.16 | — | — | — |
| — | — | — | 7 | very dark | — | — | — | — |
| — | — | — | 8 | very dark | — | — | — | — |

[a] ug/ml
[b] shades of orange

As indicated by Table 1, when the sample strip containing normal urine was aligned with the color in the wells of the standard strip, wells 1-6 of the normal urine sample strip correlated with the colors observed in wells 3-8 in the standard strip. When the colors in the two strips were aligned, in this instance by moving the sample strip down two wells relative to the standard strip, the concentration shown in the window of the device of the invention indicated 5 ug/ml HSA.

In like manner, when the color in the wells of the sample strip containing HSA-spiked urine was aligned with the standard strip colors, wells 3-8 of the albumin-spiked urine sample strip corresponded with wells 1-6 of the standard strip. After the wells were aligned with respect to color, in this instance by moving the sample strip up two wells relative to the standard strip, the value for HSA concentration as indicated in the window of the device of the invention showed that 80 ug/ml HSA was present in the albumin-spiked urine sample.

From the foregoing detailed description, it will be evident that there are a number of changes, adaptations and modifications of the present invention which come within the province of those persons skilled in the art. However, it is intended that all such variations not departing from the spirit from the invention be considered as within the scope thereof as limited solely by the claims appended hereto.

What is claimed is:

1. An analytical reader device for detecting the presence of an analyte in a sample, said device comprising:
   a fixed support member;
   a plurality of aligned standard units supported on said fixed support member and disposed generally along a line;
   a movable support member adjacent to said fixed support member;
   a plurality of aligned sample wells supported on said movable support member and disposed generally along a line adjacent and parallel to said standard units;
   said movable support member being movable along the line of said sample wells to adjust the position of said sample wells relative to said standard units to position in alignment by visual inspection at least one of said sample wells of comparable visual property related to contents therein with at least one of said standard units to thereby define a relative corresponding position;
   a dial rotatable about an axis fixed relative to said fixed support member;
   a gear mechanism which rotates said dial about the axis as said movable support member is moved relative to said fixed support member to the relative corresponding position; and
   indicating means associated with said dial for indicating the concentration of a substance in said sample wells when said movable support member is in the relative corresponding position.

2. The device of claim 1 wherein said gear mechanism comprises a rack and pinion gear system.

3. The device of claim 1 wherein said gear mechanism includes a circular gear arrangement attached to said dial and an elongated gear rack attached to said movable support member, said circular gear arrangement engaging with said elongated gear rack.

4. The device of claim 1 wherein said indicating means includes a plurality of indicia spaced concentrically on said dial.

5. The device of claim 4 wherein said indicating means includes an indicator for indicating one of said indicia based on the rotational position of said dial.

6. The device of claim 4 wherein said indicating means including a shield over said dial, said shield defining a window through which one of said indicia can be read.

7. The device of claim 1 further comprising a shield mounted over said dial and configured such that a portion of an edge of said dial is accessible to rotate said dial and thereby via said gear mechanism move said movable support member relative to said fixed support member.

8. The device of claim 1 wherein said plurality of aligned standard units comprises a plurality of aligned standard wells.

9. The device of claim 8 wherein said plurality of standard wells comprises a strip of interconnected standard wells.

10. The device of claim 1 wherein said indicating means comprises a first set of indicia in a first circular band on said dial and associated with a first substance and a second set of indicia in a second circular band concentric to said first circular band and associated with a second substance.

11. The device of claim 1 further comprising a dial support member through which said dial axis passes and fixed to said fixed support member.

12. The device of claim 1 wherein said fixed support member comprises an elongated track along which said movable support member slides.

13. The device of claim 1 wherein the comparable visual property comprises color intensity of the contents.

14. The device of claim 1 wherein the comparable visual property is directly related to the contents.

15. The device of claim 1 wherein the comparable visual property is of the contents.

16. The device of claim 1 wherein said movable support member is movable along the line of said sample wells.

17. The device of claim 1 wherein said gear mechanism has the movement thereof corresponding with the alignment of said sample wells with at least one of said standard units.

18. The device of claim 1 wherein said movable support member is structurally related to said fixed support member so as to be positioned and arranged to move along the line of said sample wells.

19. The device of claim 1 wherein the visual property comprises a visually detectable parameter that changes in relation to the concentration of the contents.

20. The device of claim 1 wherein the visual property is selected from the group consisting of color, color intensity, turbidity and opaqueness.

21. The device of claim 1 wherein said movable support member is structurally related to said gear mechanism such that alignment of said sample wells with at least one said standard unit corresponds with movement of said gear mechanism.

* * * * *